United States Patent [19]
Schwarzberg

[11] Patent Number: 5,730,143
[45] Date of Patent: Mar. 24, 1998

[54] ELECTROCARDIOGRAPHIC MONITORING AND RECORDING DEVICE

[75] Inventor: Robert Schwarzberg, Boca Raton, Fla.

[73] Assignee: Ralin Medical, Inc., Buffalo Grove, Ill.

[21] Appl. No.: 647,465

[22] Filed: May 3, 1996

[51] Int. Cl.$^6$ .................................. A61B 5/0432
[52] U.S. Cl. .............................. 128/710; 128/904
[58] Field of Search .......................... 128/696, 904, 128/903, 702, 710

[56] References Cited

U.S. PATENT DOCUMENTS

| | | | |
|---|---|---|---|
| 4,622,979 | 11/1986 | Katchis et al. | 128/904 |
| 4,889,131 | 12/1989 | Salem et al. | 128/903 |
| 5,226,424 | 7/1993 | Bible | 128/696 |
| 5,289,824 | 3/1994 | Mills et al. | 128/904 |
| 5,313,953 | 5/1994 | Yomtov et al. | 128/710 |
| 5,365,935 | 11/1994 | Righter et al. | 128/710 |

*Primary Examiner*—William E. Kamm
*Assistant Examiner*—Kennedy J. Schaetzle
*Attorney, Agent, or Firm*—Kalow, Springut & Bressler

[57] ABSTRACT

An electrocardiographic monitoring and recording device that includes continuous long-term recording with real time evaluation of the incoming data in an evaluation buffer for the occurrence of a clinically significant event. The occurrence of an event meeting programmable parameters causes the data stored in the evaluation buffer (which covers the period of time both before and after the event) to be transferred to a holding buffer and also triggers a patient alert. The patient, thus alerted, can then download the holding buffer via telephone to a central monitoring station. The patient can also manually trigger the transfer of data to the holding buffer. The monitor includes a separate long-term memory for storing up to 12-24 hours of data, which can also be down loaded.

26 Claims, 1 Drawing Sheet

ELECTROCARDIOGRAPHIC MONITORING AND RECORDING DEVICE

This invention relates to portable, wearable devices for recording and transmitting electrocardiographic data. More specifically, this invention relates to a wearable device for the selective and continuous recording of electrocardiographic data. The selective recording of data can be timed or centered around the occurrence of a clinically significant event, as detected by the device or triggered by the wearer. The data may thereafter be transferred to a holding buffer and subsequently transmitted digitally or via telephone to a remote station for evaluation. Simultaneously with the selective recording, continuous extended recording occurs, allowing for 24 hours or more of ECG data to be captured for evaluation or all or any portion.

BACKGROUND OF THE INVENTION

For a number of years, cardiac patients have been evaluated with a device known as "Holter" monitor. The patient wears a small sensor which will pick up his or hers heart signal. The signals are recorded on recording tape by the holter monitor for a 24 hour period (or other extended time). The tape is sent to a central station for evaluation by an external computer, which searches for irregularities which may have occurred during the monitored period. However, these devices have been found to be less than completely satisfactory in that the patient may not have been symptomatic during the monitored period, and therefore any recorded arrhythmias may have no clinical significance. Furthermore the recording, transmittal and subsequent evaluation of the data may cause unacceptable delays. More modern variants of Holter recorders have substituted flash memory for recording tape or provide limited onboard analysis; however, the above described problems remain.

More recently, devices known as event recorders have been employed for cardiac monitoring. These devices, which are also worn by the patient, record ECG data when triggered by the patient or by the occurrence of a clinically significant event. The recordings usually last for about 1–5 minutes and can be transmitted over ordinary telephone lines. The advantage of event recorders are extended monitoring periods (because the device is not operating continuously) and relatively quick access to the data. A disadvantage is the limited amount of electrocardiographic data available to the physicians, who are accustomed to and comfortable with the extended monitoring and extensive data provided by the Holter type devices.

Another type of device is illustrated in U.S. Pat. No. 4,622,979 (to Katehis, et al.), which is directed to an electrocardiographic monitoring device which continually monitors, and digitally stores in memory, the electrocardiograph signals of the patient. When the memory is full the new electrocardiograph data overwrites the older data. Upon the occurrence of symptoms the patient may activate a switch to halt overwriting of the data, which may then be downloaded by telephone to a central location. The device can be programmed to retain a defined time before and after activation, e.g., 40 seconds before and 20 seconds after, or 15 seconds before and 70 seconds after, etc. This device, like the event recorders described above, has the disadvantage of not providing the extensive data or extended monitoring period of Holter type devices.

Another significant disadvantage of some of these devices is that they rely on the patient to trigger the recording (or halt the overwriting of data). A clinically significant cardiac event may occur without the patient being symptomatic (e.g. the patient feels no pain) and thus no recording of the event occurs. Another common occurrence is that the event may disable the patient, e.g., the patient suffers syncope (fainting), and thus is unable to trigger a recording of the event.

The present invention is directed to overcoming the shortcomings of both Holter type and event type cardiac monitors.

SUMMARY OF THE INVENTION

The present invention is directed to an electrocardiographic monitoring and recording device that includes the continuous long-term recording of a Holter device and the selective recording of event type recorders. The selective recording permits real time evaluation of the incoming data in an evaluation buffer for the occurrence of a clinically significant event. The parameters of what constitutes a clinically significant event are adjustable and may be remotely programmable in accordance with the physicians' orders based upon the patients medical history. Upon the occurrence of an event meeting the programmed parameters, the data stored in the evaluation buffer (which can cover a period of time both before and after the event) is transferred to a holding buffer and a patient alert can be triggered. The patient can also manually trigger the transfer of data to the holding buffer. Several events could be held in this buffer. The patient can then download the holding buffer digitally or via telephone to the doctor or a central monitoring station. The monitor device of the present invention also includes a separate long-term memory for storing more data, hours before and/or after the trigger event, e.g., 12–24 hours or more of additional data, which can also be downloaded. The extended, usually continuous, recording can be terminated by the patient or by medical personnel via telephone, thus allowing any time period to be observed and evaluated in relation to documented events isolated by the selective data recording system.

BRIEF DESCRIPTION OF THE DRAWINGS

For a better understanding of the invention, reference is made to the following drawing, which is to be taken in conjunction with the Detailed Description which follows.

DETAILED DESCRIPTION OF THE PREFERRED EMBODIMENTS

Figure 1:
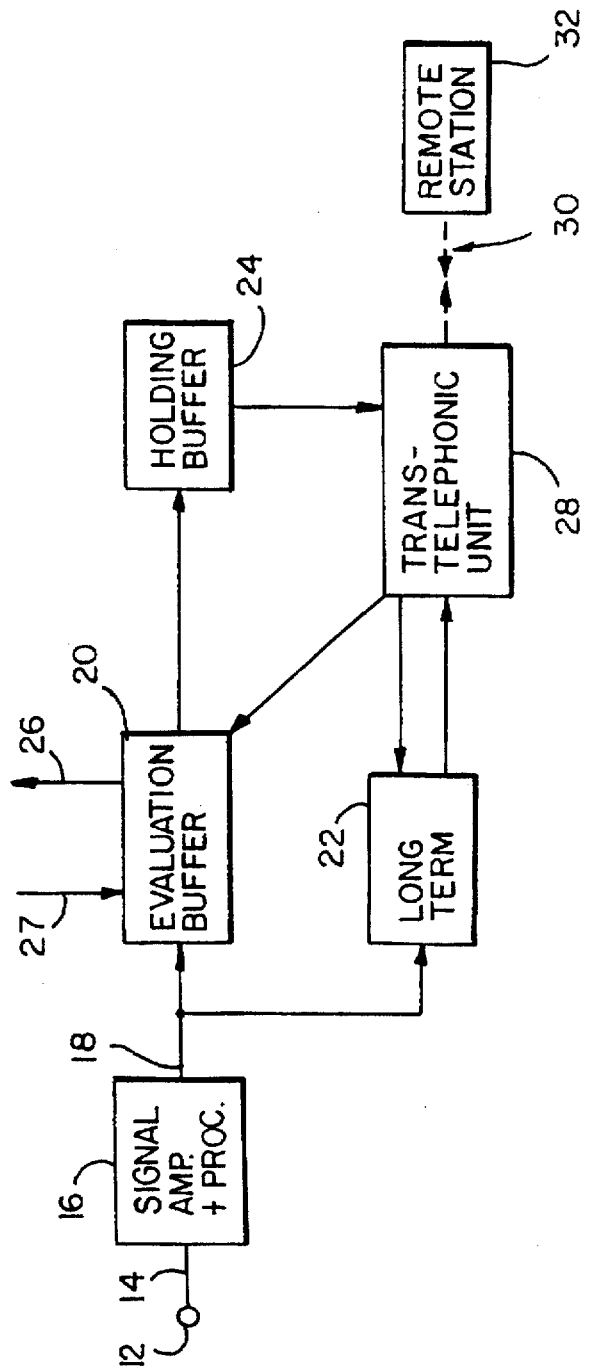
FIG. 1 is a block diagram of the electrocardiographic recording and monitoring device constructed in accordance with the present invention.

FIG. 1 illustrates the portable, wearable electrocardiographic recording and monitoring device 10 of the present invention. Device 10 includes an electrode 12 (or electrodes) for attachment to the skin of the person whose heart rhythms are to be monitored. Connecting electrode 12 to an amplifying/signal processing circuit 16 are wires 14.

Circuit 16 amplifies the weak signals from electrode 12 and removes the noise so as to provide an electrocardiograph signal 18 (e.g., a standard "QRS" waveform) for evaluation and recording by the other components of device 10. Electrode 12 and circuit 16 are standard components used in a variety of cardiac monitors. If the subsequent storage media is digital, rather than analog, circuit 16 will include suitable analog to digital circuitry. Circuit 16 also preferably includes diagnostic routines to determine that electrode 12 is in proper electrical contact with the skin of the patient so that the signals are not interrupted or attenuated. Such diagnostic circuitry may include a continuity check of electrode 12.

Electrocardiograph signal 18 is applied to two memories, a first buffer means (also referred to as an evaluation buffer) and a long-term storage means (also referred to as long-term memory or extended memory). In the drawing the memories are represented by evaluation buffer 20 and long-term memory 22, respectively. Evaluation buffer 20 may be in the form of a "flashcard", or other solid state memory, and typically will store about 1 to 10 minutes of the electrocardiograph signal 18.

The evaluation buffer is configured to overwrite the first stored data with new data from the incoming electrocardiographic signals 18. The overwriting of the electrocardiograph signals will continue until the buffer receives an activation signal to either stop overwriting or to transfer the stored data to a second buffer means (also referred to as a holding buffer) before continuing overwriting.

The long-term memory may be either solid state memory or a magnetic tape or disk, etc. recorder. Preferably, the long-term memory is solid state memory sufficient to hold at least 12 hours of EGG data, more preferably at least 24 hours of data. Moreover, the long-term memory may continuously overwrite the earliest stored data with new data, thereby being capable of operating for days. In preferred embodiments, recording by the long-term memory may be terminated by the device, by the patient via a switch on the device or by medical personnel via telephonic communication, as described in further detail below.

In one embodiment of the invention, the activation signal is manually sent to the evaluation buffer by the patient via a switch, typically when the patient feels the occurrence of a cardiac event. In the simplest form of the device, evaluation buffer then stops its overwriting and the patient must bring the evaluation buffer and the long-term memory to a remote station for further evaluation. The remote station may comprise medical personnel or an external computer which provides further analysis of the EGG data.

In more preferred embodiments of the device, the evaluation buffer upon receipt of the activation signal transfers its data to a holding buffer and then continues the overwriting until the next activation signal. In this manner selective recordings of several cardiac events may occur before transferring the data to a remote station from the holding buffer.

In other even more preferred embodiments of the invention, the activation signal may also or instead be automatic upon the occurrence of a cardiac event, thereby eliminating the need to rely on patient activation. In such embodiments, evaluation buffer 20 may incorporate a microprocessor or digital signal processor to evaluate the electrocardiograph signal in real time. The electrocardiograph signal is evaluated in relation to certain stored parameters that are used to determine if a clinically significant event has occurred. If a clinically significant event has not occurred, e.g., the preprogrammed criteria have not been met, evaluation buffer 20 overwrites the first stored data and continues to evaluate the incoming electrocardiographic signals 18. The overwriting and evaluation of the electrocardiograph signals will continue until the preprogrammed parameters are met.

If the preprogrammed parameters are met, the electrocardiographic data stored in evaluation buffer 20 will be transferred to a holding buffer 24 and a patient alert 26 will preferably be activated. Patient alert 26 may be in the form of a light or sound generator to alert the patient that an event has occurred and that holding buffer has data to be transferred to remote station 32 for further evaluation.

In addition to automatic actuation of the transfer of data to holding buffer 24, a patient operated switch 27 may also be included and used to manually transfer the data to holding buffer 24. Of course, the device may also be designed so that the automatic activation signal does not transfer the stored data but only signals the patient to manually transfer the data to the holding buffer. This would be a less desirable embodiment of the invention.

Typically, the evaluation buffer will contain about 1–10 minutes of data which will contain electrocardiograph data both before and after the triggering event. This aspect of the invention is similar to the unit shown in U.S. Pat. No. 4,622,979, whose disclosure is hereby incorporated by reference into the present disclosure. The amount of data held by the evaluation buffer after overwriting ceased or transferred to holding buffer 24 (i.e., how much pre and post event data) may be pre-programmed. As discussed above, after transfer of the data to holding buffer 24, evaluation buffer 20 may resume normal operation. The holding buffer 24 may be of such size as to permit the holding of data from several events prior to transmission for further evaluation.

Either the evaluation buffer (in embodiments where there is no holding buffer) or the holding buffer may be connected to a transtelephonic unit 28 which is used to transfer the data stored by the buffer by digital communications or telephone lines 30 to an external location or remote station 32 for further display and evaluation by an external computer or medical personnel. It is contemplated that the transmission of the data in the evaluation buffer or the holding buffer can be performed manually by the patient or automatically without reliance on the patient.

Transtelephonic unit 28 may be similar to a computer modem (and the unit shown in U.S. Pat. No. 4,622,979) in that it encodes and decodes data for transmission over telephone lines to permit two way data flow, e.g., electrocardiographic data out, and receipt of program and operational data. It is contemplated that data transmission can be in analog or digital form, and that various transmission devices may be utilized as they become available, e.g., cellular devices, satellite or cable transmission, etc.

In addition to transmitting the data in the evaluation or holding buffer, unit 28 (or a separate unit) may also permit downloading of some or all data from the 12–24 hour long-term memory 22 and can receive programming commands, e.g., for re-programming the parameters of evaluation buffer 20 or terminating the recording of the long-term memory.

Remote station 32 may include a computer and storage for the data downloaded from device 10 and can output commands to device 10. For example, station 32 may be programmed to request that, in addition to the data contained in holding buffer 24, a preprogrammed amount of data from long-term memory 22 be also sent by unit 28 (or another unit) to remote site 32. The request for additional data can be based on the identity of the patient, the particular cardiologist involved or further analysis by remote site 32 of the data received from buffer 24.

In addition to the downloading of data to remote site 32, transtelephonic unit 28 may also be used to reprogram the parameters used in the evaluation buffer 20. Evaluation buffer 20 can be programmed to trigger upon the occurrence of a number of clinically significant events. Among the significant events are tachycardia (rapid heartbeat), bradycardia (slow heartbeat), a pause in heartbeat, and any other form of arrhythmia. A number of algorithms for evaluating electrocardiograph signals are commercially available and these or new algorithms may be used in the signal processing of evaluation buffer 20 to trigger the transfer of the contents to holding buffer 24.

Additional elements for the manufacture or use of devices in accordance with the present invention are known in the industry, e.g., power supply, apparatus to permit the carrying of the device, etc. The present disclosure is not intended as a treatise on cardiac monitors and readers are referred to appropriate, available texts in the field for additional information.

The invention has been described with respect to preferred embodiments. However, as those skilled in the art will recognize, modifications and variations in the specific details which have been described and illustrated may be resorted to without departing from the spirit and scope of the invention as defined in the appended claims.

What is claimed is:

1. A portable electrocardiographic monitoring device, for attachment to a patient, comprising:
   an electrical circuit means for outputting a signal representative of heart rhythms of the patient;
   an evaluation buffer means for storing the signal output from said electrical circuit means and for continuously overwriting the earliest stored signals after its storage capacity is reached, said evaluation buffer means having a predetermined storage capacity;
   a long term storage means for storing the sisal output from said electrical circuit means simultaneously with said evaluation buffer means storing said signal output, said long term storage means having a storage capacity greater than that of said evaluation buffer; and
   a signaling means for producing an activation signal which causes the evaluation buffer means to cease overwriting or to transfer its stored signals.

2. A monitoring device of claim 1 further comprising a holding buffer means for receiving and storing data transferred from said evaluation buffer means, said evaluation buffer means transferring its stored signals to said holding buffer means after receiving said activation signal.

3. A monitoring device of claim 2, wherein the signaling means comprises a signal processing means for evaluating the signals representing the heart rhythms of the patient, said signal processing means stores certain parameters therein, compares said signals representing the heart rhythm with said stored parameters and, based on results of said comparison, outputs said activation signal, said activation signal causing said first buffer means to transfer said stored signals to said holding buffer means.

4. A monitoring device of claim 3 further comprising a transtelephonic means for transferring the contents of said holding buffer means to an external location.

5. The monitoring device of claim 4, wherein said transtelephonic means includes means for altering the parameters stored in said signal processing means.

6. A monitoring device of claim 5 further comprising a transtelephonic means for transferring the contents of said holding buffer means to an external location, for transferring the contents of the long term storage means to said external location and for altering the parameters stored in said signal processing means upon receipt of electronic commands from said external location.

7. A monitoring device of claim 3 further comprising a transtelephonic means for transferring the contents of said evaluation buffer to an external location and for transferring the contents of the long term storage means.

8. A monitoring device of claim 1, wherein the signaling means comprises a signal processing means for evaluating the signals representing the heart rhythms of the patient, said signal processing means stores certain parameters therein, compares said signals representing the heart rhythms with said stored parameters and, based on results of said comparison, outputs said activation signal.

9. The monitoring device of claim 8 further comprising means for alerting the patient that the activation signal has occurred.

10. The monitoring device of claim 8, wherein said signal processing means include means for triggering the activation signal when the patient's heartbeat is arrhythmic.

11. A monitoring device of claim 1 further comprising a transtelephonic means for transferring the contents of said evaluation buffer means to an external location.

12. The monitoring device of claim 1, wherein the signaling means comprises an activation means for permitting the patient to generate the activation signal.

13. The monitoring device of claim 1, wherein said evaluation buffer means and said long-term storage means comprise solid state memory and said signals are stored in digital form.

14. A monitoring device of claim 13, wherein said long term storage means includes overwriting means for continuously overwriting the earliest stored signals after the storage capacity is reached.

15. The monitoring device of claim 1, wherein the storage capacity of the evaluation buffer means is between about 1 minute and about 15 minutes.

16. The monitoring device of claim 1, wherein the storage capacity of the long-term storage means is between about 10 hours and about 24 hours.

17. A monitoring device of claim 1 wherein said long-term storage means includes means for continuously storing the signal output from said electrical circuit means.

18. A portable electrocardiographic monitoring device, for attachment to a patient, comprising:
   an electrical circuit means for outputting a signal representative of heart rhythms of the patient;
   an evaluation buffer means for storing the signal output from said electrical circuit means, and for continuously overwriting the earliest stored signals after its storage capacity is reached, said storage capacity being predetermined;
   a holding buffer means for receiving and storing data transferred tom said evaluation buffer means, said evaluation buffer means transferring its stored data to said holding buffer means after receiving an activation signal;
   a signal processing means for evaluating the signals representing the heart rhythms of the patient, said signal processing means stores certain parameters therein, compares said signals representing the heart rhythms with said stored parameters and, based on results of said comparison, outputs said activation signal;
   a long term storage means for storing signals representative of the heart rhythms of the patient, said long term storage means having a storage capacity greater than that of said evaluation buffer.

19. The monitoring device of claim 18 further comprising means for alerting the patient that the activation signal has occurred and that stored data are in the holding buffer means.

20. The monitoring device of claim 18 further comprising a switch permitting the patient to generate an activation signal.

21. A monitoring device of claim 18, wherein the storage capacity of the evaluation buffer means is between about 1 minute and about 15 minutes and the storage capacity of the long term storage means is between about 12 hours and about 24 hours, the evaluation buffer means and the long term storage means comprising solid state memory and the long term storage means includes overwriting means for continuously overwriting the earliest stored signals after its storage capacity is reached.

22. A portable electrocardiographic monitoring device, for attachment to a patient, comprising:

an electrical circuit means for outputting a signal representative of heart rhythms of the patient;

an evaluation buffer means for storing the signal output from said electrical circuit means and for continuously overwriting the earliest stored signals after its storage capacity is reached, said storage capacity being predetermined;

a long term storage means for storing the signal output from said electrical circuit means, said long term storage means having a storage capacity greater than that of said evaluation buffer;

a signaling means for producing an activation signal which causes the evaluation buffer means to cease overwriting or to transfer its stored signals; and a holding buffer means for receiving and storing data transferred from said evaluation buffer means, said evaluation buffer means transferring its stored signals to said holding buffer means after receiving said activation signal.

23. A monitoring device of claim 22 further comprising a transtelephonic means for transferring the contents of said evaluation buffer means to an external location.

24. A monitoring device of claim 22 further comprising a transtelephonic means for transferring the contents of said holding buffer means to an external location.

25. A monitoring device of claim 22 further comprising a transtelephonic means for transferring the contents of said evaluation buffer and for transferring the contents of the long term storage means to an external location.

26. The monitoring device of claim 25, wherein said transtelephonic means includes means for altering the parameters stored in said signal processing means.

* * * * *

(12) EX PARTE REEXAMINATION CERTIFICATE (8176th)
United States Patent
Schwarzberg

(10) Number: US 5,730,143 C1
(45) Certificate Issued: Apr. 26, 2011

(54) ELECTROCARDIOGRAPH MONITORING AND RECORDING DEVICE

(75) Inventor: Robert Schwarzberg, Boca Raton, FL (US)

(73) Assignee: Lifewatch Services Inc., Rosemont, IL (US)

Reexamination Request:
No. 90/010,868, Feb. 19, 2010

Reexamination Certificate for:
Patent No.: 5,730,143
Issued: Mar. 24, 1998
Appl. No.: 08/647,465
Filed: May 3, 1996

(51) Int. Cl.
*A61B 5/0432* (2006.01)

(52) U.S. Cl. .................................. 600/523; 128/904
(58) Field of Classification Search ............. None
See application file for complete search history.

(56) References Cited

U.S. PATENT DOCUMENTS

| | | |
|---|---|---|
| 3,776,228 A | 12/1973 | Semler |
| 3,779,249 A | 12/1973 | Semler |
| 4,364,397 A | 12/1982 | Citron et al. |
| 4,531,527 A | 7/1985 | Reinhold et al. |
| 4,572,182 A | 2/1986 | Royse |
| 4,583,553 A | 4/1986 | Shah et al. |
| 4,625,730 A | 12/1986 | Fountain et al. |
| 4,803,625 A | 2/1989 | Fu et al. |
| 4,920,489 A | 4/1990 | Hubelbank et al. |
| 4,938,228 A | 7/1990 | Righter et al. |
| 4,958,641 A | 9/1990 | Digby et al. |
| 4,967,756 A | 11/1990 | Hewitt |
| 4,977,899 A | 12/1990 | Digby et al. |
| 5,012,814 A | 5/1991 | Mills et al. |
| 5,058,597 A | 10/1991 | Onoda et al. |
| 5,090,418 A | 2/1992 | Squires et al. |
| 5,111,396 A | 5/1992 | Mills et al. |
| 5,128,552 A | 7/1992 | Fang et al. |
| 5,181,519 A | 1/1993 | Bible |
| 5,191,891 A | 3/1993 | Righter |
| 5,201,321 A | 4/1993 | Fulton |
| 5,205,295 A | 4/1993 | Del Mar et al. |
| 5,226,425 A | 7/1993 | Righter |
| 5,238,001 A | 8/1993 | Gallant et al. |
| D341,659 S | 11/1993 | Homayoun et al. |
| 5,304,186 A | 4/1994 | Semler et al. |
| 5,317,269 A | 5/1994 | Mills et al. |
| 5,333,616 A | 8/1994 | Mills et al. |
| 5,339,824 A | 8/1994 | Engira |
| 5,343,869 A | 9/1994 | Pross et al. |
| 5,343,870 A | 9/1994 | Gallant et al. |
| 5,348,008 A | 9/1994 | Bornn et al. |
| 5,351,695 A | 10/1994 | Mills et al. |
| 5,365,935 A | 11/1994 | Righter et al. |
| 5,417,222 A | 5/1995 | Dempsey et al. |
| 5,467,773 A | 11/1995 | Bergelson et al. |
| 5,518,001 A | 5/1996 | Snell |

(Continued)

OTHER PUBLICATIONS

Gomez, "A Telemedicine Distributed Decision—Support System for Diabetes Management," IEEE, Oct. 29, 1992, pp. 1238–1239, USA.

(Continued)

*Primary Examiner*—Jeffrey R. Jastrzab

(57) ABSTRACT

An electrocardiographic monitoring and recording device that includes continuous long-term recording with real time evaluation of the incoming data in an evaluation buffer for the occurrence of a clinically significant event. The occurrence of an event meeting programmable parameters causes the data stored in the evaluation buffer (which covers the period of time both before and after the event) to be transferred to a holding buffer and also triggers a patient alert. The patient, thus alerted, can then download the holding buffer via telephone to a central monitoring station. The patient can also manually trigger the transfer of data to the holding buffer. The monitor includes a separate long-term memory for storing up to 12-24 hours of data, which can also be down loaded.

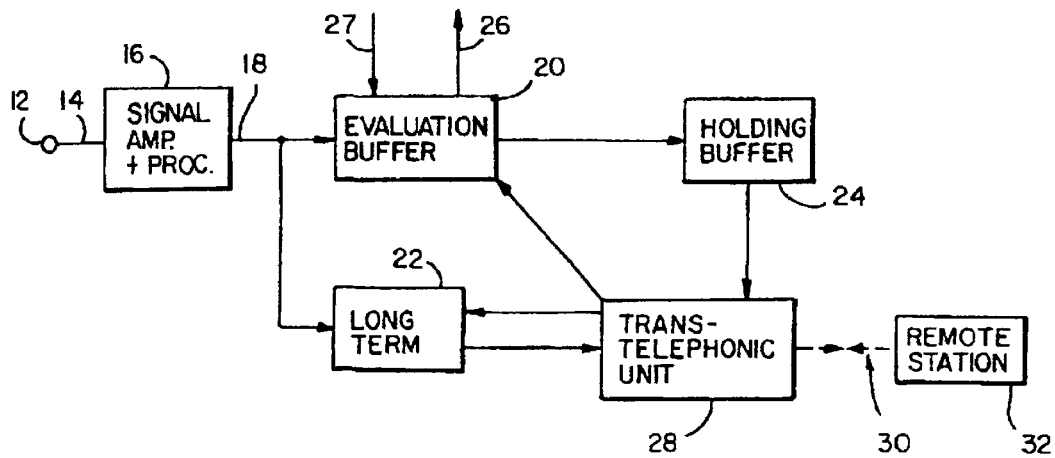

U.S. PATENT DOCUMENTS

| | | | |
|---|---|---|---|
| 5,522,396 | A | 6/1996 | Langer et al. |
| D372,785 | S | 8/1996 | Sabri et al. |
| 5,544,661 | A | 8/1996 | Davis et al. |
| 5,581,369 | A | 12/1996 | Righter et al. |
| D377,983 | S | 2/1997 | Sabri et al. |
| 5,613,495 | A | 3/1997 | Mills et al. |
| 5,652,570 | A | 7/1997 | Lepkofker |
| 5,678,562 | A | 10/1997 | Sellers |
| 5,701,894 | A | 12/1997 | Cherry et al. |
| 5,704,364 | A | 1/1998 | Saltzstein et al. |
| 5,724,025 | A | 3/1998 | Tavori |
| 5,772,586 | A | 6/1998 | Heinonen |
| 5,840,020 | A | 11/1998 | Heinonen et al. |
| 5,929,761 | A | 7/1999 | Van der Laan et al. |
| 5,941,829 | A | 8/1999 | Saltzstein et al. |
| 6,072,396 | A | 6/2000 | Gaukel et al. |
| 6,083,248 | A | 7/2000 | Thompson |
| 6,100,806 | A | 8/2000 | Gaukel et al. |
| 7,596,405 | B2 | 9/2009 | Kurzweil et al. |

OTHER PUBLICATIONS

Wiesspeiner & Wu, "Multichannel Ambulatory Monitoring of Circulation Related Biosignals," IEEE, Sep. 23, 1991, pp. 457–460, USA.

Sony, "Operating Instructions, Sony Clie Personal Entertainment Organizer PEG–NX70V, PEG NX60," 2002, pp. 1–100.

077.00—Lifewatch's Memorandum in Opposition to Defendant's Motion for Partial Summary Judgment of Non–Infringement; *Lifewatch v. Braemar (IL)*; Civil Action No. 09–06001; Filed Jul. 30, 2010.

077.01—Plaintiff's Local Rule 56.1 Statement of Additional Facts Requiring Denial of Defendants' Motion for Summary Judgment; *Lifewatch v. Braemar (IL)*; Civil Action No. 09–06001; Filed Jul. 30, 2010.

077.02—Plaintiff's Local Rule 56.1 Response to Defendants' Local Rule 56.1 "Statement of Facts" in Support of Defendant's Motion for Summary Judgment; *Lifewatch v. Braemar (IL)*; Civil Action No. 09–06001; Filed Jul. 30, 2010.

077.03—Declaration of Jeremy P. Oczek in Support of Lifewatch's Opposition to Defendants' Motion for Partial Summary Judgment of Non–Infringement; *Lifewatch v. Braemar (IL)*; Civil Action No. 09–06001; Filed Jul. 30, 2010.

077.05—Exhibit B to Oczek; *Lifewatch v. Braemar (IL)*; Civil Action No. 09–06001; Filed Jul. 30, 2010.

077.06—Exhibit C to Oczek; *Lifewatch v. Braemar (IL)*; Civil Action No. 09–06001; Filed Jul. 30, 2010.

077.12—Exhibit I to Oczek; *Lifewatch v. Braemar (IL)*; Civil Action No. 09–06001; Filed Jul. 30, 2010.

077.13—Exhibit J to Oczek; *Lifewatch v. Braemar (IL)*; Civil Action No. 09–06001; Filed Jul. 30, 2010.

077.14—Exhibit K to Oczek; *Lifewatch v. Braemar (IL)*; Civil Action No. 09–06001; Filed Jul. 30, 2010.

077.15—Exhibit L to Oczek; *Lifewatch v. Braemar (IL)*; Civil Action No. 09–06001; Filed Jul. 30, 2010.

077.16—Declaration of Dr. Earl Sacerdoti; *Lifewatch v. Braemar (IL)*; Civil Action No. 09–06001; Filed Jul. 30, 2010.

077.17—Exhibit A to Sacerdoti; *Lifewatch v. Braemar (IL)*; Civil Action No. 09–06001; Filed Jul. 30, 2010.

077.18—Exhibit B to Sacerdoti; *Lifewatch v. Braemar (IL)*; Civil Action No. 09–06001; Filed Jul. 30, 2010.

077.19—Exhibit C to Sacerdoti; *Lifewatch v. Braemar (IL)*; Civil Action No. 09–06001; Filed Jul. 30, 2010.

077.20—Exhibit D to Sacerdoti; *Lifewatch v. Braemar (IL)*; Civil Action No. 09–06001; Filed Jul. 30, 2010.

077.21—Exhibit E to Sacerdoti; *Lifewatch v. Braemar (IL)*; Civil Action No. 09–06001; Filed Jul. 30, 2010.

082.00—Defendants' Reply Memorandum in Support of Motion for Summary Judgment; *Lifewatch v. Braemar (IL)*; Civil Action No. 09–06001; Filed Aug. 10, 2010.

082.01—Defendant's Response to Plaintiff's Local Rule 56.1 Statement of Additional Facts; *Lifewatch v. Braemar (IL)*; Civil Action No. 09–06001; Filed Aug. 10, 2010.

082.02—Declaration of Robert Shwarzberg; *Lifewatch v. Braemar (IL)*; Civil Action No. 09–06001; Filed Aug. 10, 2010.

086.00—Lifewatch's Motion for Leave to File A Sur–Reply Brief in Connection with Defendants' Motion for Partial Summary Judgment; *Lifewatch v. Braemar (IL)*; Civil Action No. 09–06001; Filed Aug. 20, 2010.

086.01—Exhibit A; *Lifewatch v. Braemar (IL)*; Civil Action No. 09–06001; Filed Aug. 20, 2010.

086.02—Exhibit I; *Lifewatch v. Braemar (IL)*; Civil Action No. 09–06001; Filed Aug. 20, 2010.

088.00—Lifewatch's Motion to Disqualify Robert Schwarzberg from Serving as an Expert and Strike Declaration; *Lifewatch v. Braemar (IL)*; Civil Action No. 09–06001; Filed Aug. 25, 2010.

088.01—Exhibit A; *Lifewatch v. Braemar (IL)*; Civil Action No. 09–06001; Filed Aug. 25, 2010.

088.02—Exhibit B; *Lifewatch v. Braemar (IL)*; Civil Action No. 09–06001; Filed Aug. 25, 2010.

094.00—Defendant's Opposition to LW's Motions to Disqualify R. Schwarzberg from Serving as an Expert; *Lifewatch v. Braemar (IL)*; Civil Action No. 09–06001; Filed Sep. 14, 2010.

094.01—Declaration of John L. Krenn); *Lifewatch v. Braemar (IL)*; Civil Action No. 09–06001; Filed Sep. 14, 2010; *Lifewatch v. Braemar (IL)*; Civil Action No. 09–06001; Filed Sep. 14, 2010.

095.00—LW's Reply ISO Motion to Disqualify R. Schwarzberg from Serving as an Expert; *Lifewatch v. Braemar (IL)*; Civil Action No. 09–06001; Filed Sep. 21, 2010.

095.01—Exhibit A; *Lifewatch v. Braemar (IL)*; Civil Action No. 09–06001; Filed Sep. 21, 2010.

Order Granting LW's Motion to Disqualify Dr. Schwarzberg from Serving as an Expert and Strike Declaration; *Lifewatch v. Braemar (IL)*; Civil Action No. 09–06001; Filed Sep. 28, 2010.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 18 and 22 are determined to be patentable as amended.

Claims 2-17, 19-21 and 23-26, dependent on an amended claim, are determined to be patentable.

1. A portable electrocardiographic monitoring device, for attachment to a patient, comprising:
   an electrical circuit means for outputting a signal representative of heart rhythms of the patient;
   an evaluation buffer means for storing the signal output from said electrical circuit means and for continuously overwriting the earliest stored signals after its storage capacity is reached, said evaluation buffer means having a predetermined storage capacity;
   a long term storage means for the [sisal] *same signal* output from said electrical circuit means simultaneously with said evaluation buffer means storing said signal output, said long term storage means having a storage capacity greater than that of said evaluation buffer; and
   a signaling means for producing an activation signal which causes the evaluation buffer means to cease overwriting or to transfer its stored signals.

18. A portable electrocardiographic monitoring device, for attachment to a patient, comprising:
    an electrical circuit means for outputting a signal representative of heart rhythms of the patient;
    an evaluation buffer means for storing the signal output from said electrical circuit means, and for continuously overwriting the earliest stored signals after its storage capacity is reached, said storage capacity being predetermined;
    a holding buffer means for receiving and storing data transfered [tom] *from* said evaluation buffer means, said evaluation buffer means transferring its stored data to said holding buffer means after receiving an activation signal;
    a signal processing means for evaluating the signals representing the heart rhythms of the patient, said signal processing means stores certain parameters therein, compares said signals representing the heart rhythms with said stored parameters and, based on results of said comparison, outputs said activation signal;
    a long term storage means for storing [signals representative of the heart rhythms of the patient] *the same signal output from said electrical circuit means stored in said evaluation buffer means*, said long term storage means having a storage capacity greater than that of said evaluation buffer.

22. A portable electrocardiographic monitoring device, for attachment to a patient, comprising:
    an electrical circuit means for outputting a signal representative of heart rhythms of the patient;
    an evaluation buffer means for storing the signal output from said electrical circuit means and for continuously overwriting the earliest stored signals after its storage capacity is reached, said storage capacity being predetermined;
    a long term storage means for the *same* signal output from said electrical circuit means *that is stored in said evaluation buffer means*, said long term storage means having a storage capacity greater than that of said evaluation buffer;
    a signaling means for producing an activation signal which causes the evaluation buffer means to cease overwriting or to transfer its stored signals; and
    a holding buffer means for receiving and storing data transferred from said evaluation buffer means, said evaluation buffer means transferring its stored signals to said holding buffer means after receiving said activation signal.

* * * * *